United States Patent [19]

Sobieralski

[11] Patent Number: 4,724,051

[45] Date of Patent: Feb. 9, 1988

[54] IMPURE ZINC POWDER, PREPARATION THEREOF, AND USE AS A SELECTIVE REDUCTANT FOR PENTACHLOROPYRIDINE

[75] Inventor: Theodore J. Sobieralski, Antioch, Calif.

[73] Assignee: The Dow Chemical Company, Midland, Mich.

[21] Appl. No.: 925,440

[22] Filed: Oct. 31, 1986

Related U.S. Application Data

[62] Division of Ser. No. 715,329, Mar. 25, 1985, Pat. No. 4,640,712.

[51] Int. Cl.⁴ ............................................. C25D 3/58
[52] U.S. Cl. .............................. 204/10; 75/251; 204/44.2; 204/44.4
[58] Field of Search .................... 204/44.2, 44.4, 10

[56] References Cited

U.S. PATENT DOCUMENTS

| 4,064,033 | 12/1977 | Dekeister | 204/10 |
| 4,120,758 | 10/1978 | Rippere | 204/10 |
| 4,597,838 | 7/1986 | Bammel | 204/44.2 |

Primary Examiner—Peter D. Rosenberg

[57] ABSTRACT

Powders consisting essentially of zinc but having lead contents of from about 1000 to about 30,000 ppm can readily be produced by electrolysis of lead-containing, zinc halide solutions and are superior reductants for the preparation of symmetrical tetrachloropyridine from pentachloropyridine.

20 Claims, 3 Drawing Figures

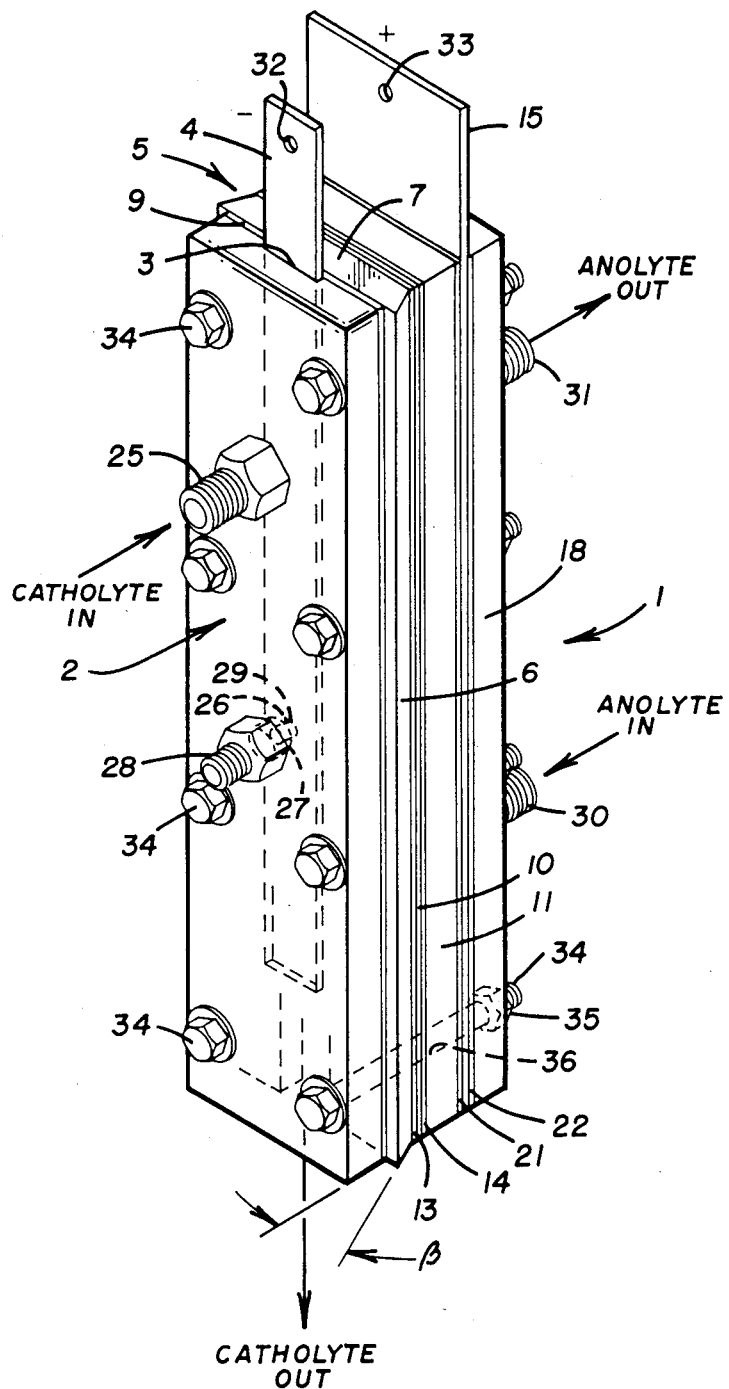

IMPURE ZINC POWDER, PREPARATION THEREOF, AND USE AS A SELECTIVE REDUCTANT FOR PENTACHLOROPYRIDINE

CROSS-REFERENCE TO RELATED APPLICATION

This is a divisional, of application Ser. No. 715,329, filed Mar. 25, 1985, now U.S. Pat. No. 4,640,712.

BACKGROUND OF THE INVENTION

Zinc powder is used for a variety of purposes in the chemical and metallurgical industries. One chemical use is in various reductions (in which the zinc is oxidized to $Zn^{2+}$, i.e., converted to a zinc halide or oxide, etc.). Conventional wisdom is to the effect that the purer the zinc, the more effective or "active" it is as a reductant.

Zinc powders (including "dusts") are prepared commercially by electrolytic deposition from neutral, weakly acid or basic solutions of zinc salts—most notably, solutions derived from ores which include zinc minerals. Deposition of the zinc in a form which can readily be removed and converted to a powder is an obvious desideratum. To this end, the use of various additives, including ions of foreign metals, has been tried.

It is taught in *Electrodeposition of Metal Powders*, A. Calusaru, Ch XVI; Elsevier Pub. (1979), Materials Science Monograph 3, that some metal ions do favor deposition of zinc in the form of a sponge (which can be readily converted to a powder) but that the activity of the zinc is lowered by inclusion of the added metals (as co-electrolysis products).

It is further taught that zinc is easily deposited from weakly acid solutions in sponge form at low current densities (0.4 A/dm$^2$ = 0.0025 A/in$^2$) but formation of compact deposits is favored by higher current densities.

Also, according to the latter reference, powdery zinc deposits may be obtained (at low current densities) by electrolysis of alkaline solutions of zinc (as zincates, that is) without the use of additives and the zinc produced is more active than zinc produced from neutral or acidic solutions.

Zinc powders of several particle size ranges are listed in the 1983/84 Alfa Catalog (Morton Thiokol, Inc.). Considering only metals, the zinc contents of these powders range from 99.9 to 99.9995%. In other words, the maximum proportion of the total metals present which could be lead range from 5 to 1000 ppm. It is believed that the latter figure is typically a maximum for prior art zinc in powder form.

There is room for improvement in the production of zinc powders, in at least two aspects. If higher current densities could be attained in the productions of zinc powders under acid conditions, acidic ore leaches could be better utilized for this purpose; also waste streams, such as acidic $ZnCl_2$ solutions formed in reductions of C-Cl groups with zinc, could be recycled economically. If the zinc powders could be made more selective as reductants for polyhalo compounds, such reductions could be carried out more efficiently and with less co-generation of over-reduction products. This latter improvement is particularly to be desired for production of 2,3,5,6-tetrachloropyridine—an important commercial intermediate—from pentachloropyridine.

OBJECTS OF THE INVENTION

A principal object of the present invention is to provide a zinc powder which is more efficient and selective as a reductant for polyhalo compounds.

An ancillary object is to provide a method for producing such a zinc powder from acidic $Zn^{2+}$ solutions.

Another object is to make economically feasible the recycling of acidic $Zn^{2+}$ waste streams.

A further object is to produce zinc powders from acidic $Zn^{2+}$ solutions at higher current densities than have been previously been considered suitable.

An additional object is to more efficiently utilize the $Zn^{2+}$ contents of acidic ore leaches.

It is also an object to effect an improvement in the method of 2,3,5,6-tetrachloropyridine production which comprises the reduction of pentachloropyridine with zinc dust in non-basic media.

Yet another object is to provide a simple type of electrolytic cell in which zinc may be continuously deposited on and removed from the cathode.

Still other objects will be made apparent to those knowledgeable in the art by the following specifications and claims.

SUMMARY OF THE INVENTION

It has been found that the foregoing objects can be achieved through electroreduction, under certain conditions, of $Zn^{2+}$ in aqueous solutions comprising lead ions in amounts such that the resulting metal deposit consists essentially of zinc but contains more than 1000 ppm (parts per million) of lead.

Powders consisting essentially of zinc and containing more than 1000 ppm of lead are believed to constitute a novel composition of matter which is unpredictably superior as a reductant for the selective reduction of pentachloropyridine ("PCP") to 2,3,5,6-tetrachloropyridine (symmetrical tetrachloropyridine, or "sym-tet"). The zinc content must be at least high enough so that the powder exhibits the essential property of being a reductant for PCP. Preferably, the powder contains less than 30,000 parts of lead per million parts of zinc.

The use, as a reductant, of a zinc powder containing more than 1000 ppm of lead is a process aspect of the invention.

The invention, in the zinc powder preparation aspect, may be more precisely defined as the method of preparing the powder which comprises:

a. providing an electrolytic cell which includes a cathode, an anode and an ion-permeable or porous member separating the cell into cathode and anode compartments, b. charging to the anode compartment an from about 1.5 to about 5 molar aqueous zinc dihalide solution and charging to said cathode compartment an from about 0.07 to about 0.7 molar aqueous zinc dihalide solution containing from about 1000 to about 30,000 parts by weight of lead ions per million parts of zinc, and c. applying across said cell a D.C. potential such as to establish and maintain a cathode potential within the range of from about −2 to −1 volts, relative to a saturated calomel reference electrode, and a cathodic current density of about 165 or more mA/cm$^2$, thereby forming on the cathode a friable zinc deposit which can be removed by impingent thereon of a flowing liquid.

In preferred versions of the latter process:
(1) the zinc dihalide in the anolyte is the same as that in the catholyte,
(2) anolyte is from about 2 to about 3 molar in the zinc dihalide,
(3) the catholyte is from about 0.3 to about 0.4 molar in the zinc dihalide and, advantageously, includes an ionizeable halide other than said diahlide,
(4) the current density is not greater than 330 mA/Cm$^2$,
(5) catholyte solution is intermittently caused to flow past and impinge against said zinc deposit with a force sufficient to remove it from the cathode,
(6) the zinc dihalide is ZnCl$_2$,
(7) the cathode is stainless steel or, more preferably, aluminum, and/or
(8) the anode is ruthenium oxide on titanium.

The cell employed in the present process is a separate invention (of the present inventor) in its own right.

The term anode or cathode, as used herein, refers either to a monolithic electrode or a surface layer in a composite electrode.

BRIEF DESCRIPTION OF DRAWINGS

An electrolytic cell employed in the practice of the present invention is shown in FIGS. 1 and 1A as perspective views of the cell in assembled and "exploded" forms, respectively.

DETAILED DESCRIPTION

Figure 1A:
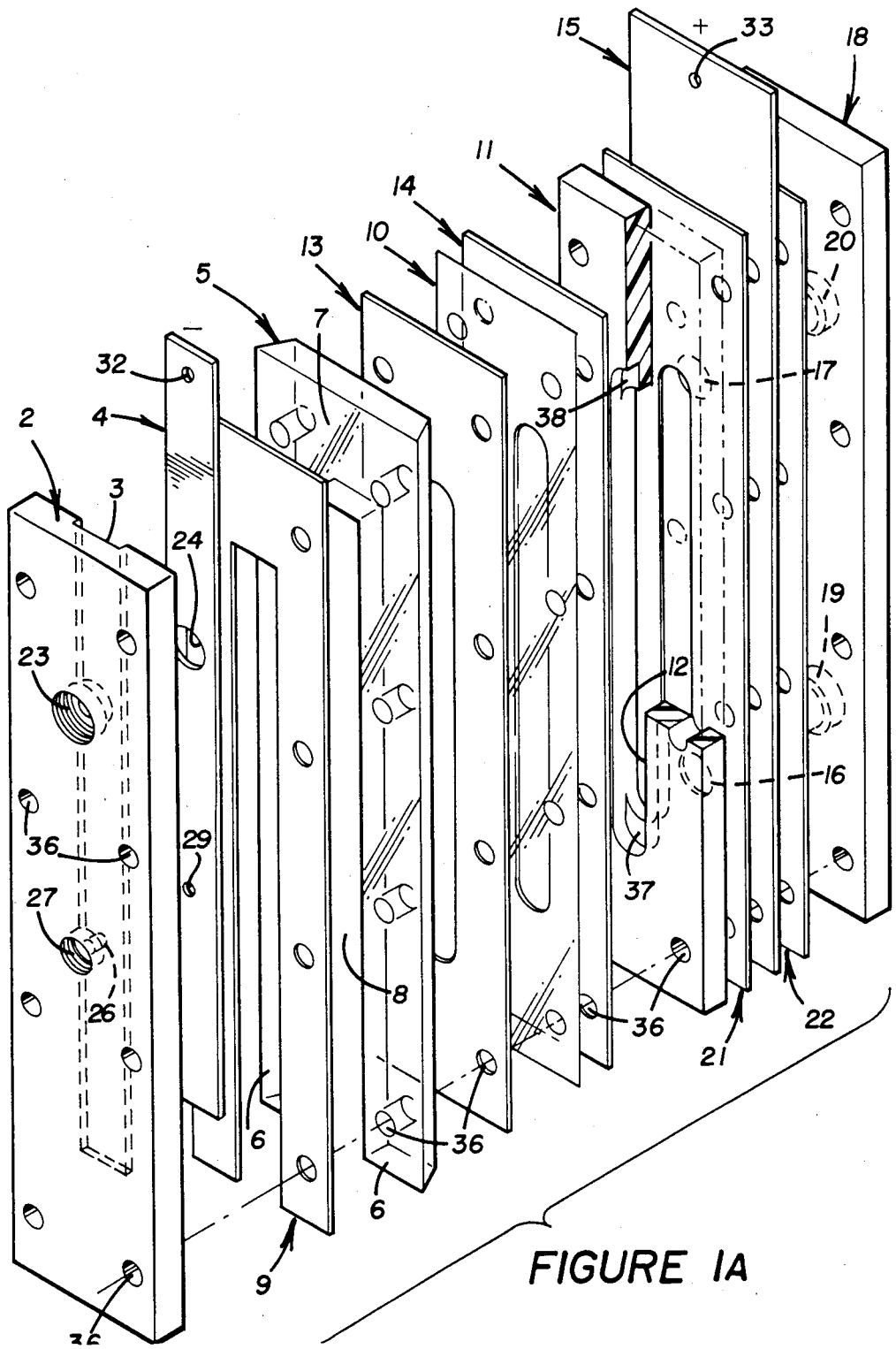

Powders within the ambit of the present composition invention are those in which the particles consist essentially of zinc and contain more than 1000 parts of lead per million parts of zinc. Advantageously, any other components of the particles are also metals. Preferably, less than 5 parts per million of materials other than zinc and lead are present in the particles. Particles of the latter kind containing from about 5000 to about 30,000 ppm of lead are more preferred and those containing from about 15,000 to about 25,000 are particularly preferred. Such powders which have been formed in the presence of water and kept wet since formed are preferred for use as PCP reductants.

Mixtures of the powder particles of the invention with other materials, said mixtures having substantially the same chemical properties as said particles, are also within the ambit of the invention. That is, the other material—a liquid, a matrix resin or particles of a different composition, for example—may effect the powder of the invention as a diluent and/or as a moderator, retardant or activator but does not adversely effect the chemical properties of the powder particles to an intolerable extent.

Agitation

The most practical procedure for carrying out the zinc preparation involves agitation of both the catholyte and anolyte within their respective compartments. Agitation of the catholyte is done, intermittently, in such a way as to create a flow pattern which removes the zinc deposit from at least the immediate vicinity of the cathode. Preferably, the catholyte is agitated by means of a circulation pump and the catholyte stream enters the cell at a velocity such that it impinges on the zinc deposit in turbulent flow; the loosened zinc particles are allowed to settle in the cell (out of further contact with the cathodic electrode) or, preferably, are swept out of the cell by the exiting catholyte stream. The simplest and most convenient way of doing this is to make the catholyte compartment open-bottomed and to position the cell in a sump from which catholyte is withdrawn, at an upper level, by the pump. The zinc particles separate from the exiting stream as it mixes with the relatively quiescent main body of the catholyte and settle to the bottom of the sump.

Removing the zinc from the cell in a flowing liquid stream helps to break up the sponge into a powder but additional washing and agitation may be required to complete this step of the process. (It is to be noted that "sponge" formation per se does not guarantee easy conversion of the zinc to a powder. Several different process variables effect the friability of the zinc deposit.)

The zinc at the bottom of the sump of course can be removed without interrupting the operation, by any of several expedients which will be apparent to those knowledgeable in the art.

The anolyte need not be agitated at all. However, it is highly preferred that it be circulated throughout the course of the reaction, particularly when the process is operated in a continuous mode; this permits removal of evolved gases from the anolyte in a separate sump.

Zinc Dihalides

The most practical zinc dihalides for the purposes of the present invention are ZnBr$_2$ and ZnCl$_2$, particularly the latter. Even a saturated solution of ZnF$_2$ in water has so low a concentration as to be impractical for use as an anolyte. ZnI$_2$ has adequate solubility but is quite expensive.

Z$_n$X$_2$

As indicated earlier herein, the concentration of the zinc dihalide(s) in the catholyte can range from about 0.07 to about 0.7 molar but preferably is within the range of from about 0.1 to about 0.2 molar. In the anolyte, the concentration of zinc dihalide(s) can range from about 1.5 to about 5 molar (the latter value corresponding to saturation for ZnCl$_2$ at room temperature) but preferably is within the range of from about 2 to about 3 molar.

Oxidation Product

The oxidation product formed at the anode can be either a halogen or oxygen, depending on the relative overpotentials of the anode for them, and on the halide concentration. That is, either $2X^- - 2e \rightarrow X_2$ or $4H_2O \rightarrow 4H^+ + 4OH^-$ and $4HO^- - 4e \rightarrow 2H_2O + O_2$. In the latter case, four equivalents of base must be added to the anolyte to neutralize the H$^+$. If the halogen formed is chlorine, it will be a gas at ordinary temperatures and can readily be separated from the anolyte. If the halogen is bromine, cell (or sump) temperatures at least as high as the boiling point of bromine (about 59° C. at 760 mmHg) can be employed to the same end. In any case, the halogen is the preferred oxidation product.

Cathode Material

The cathode material can be any otherwise suitable, electroconductive material which does not detrimentally effect the operation of the process or the properties of the produced zinc to an intolerable extent. Such materials include aluminum, nickel, platinum, palladium, gold and stainless steel—the latter (the 300 series, in particular) being preferred and aluminum being more preferred, being more electroconductive.

Anode Material

The anode material also can be any otherwise suitable, electroconductive material which does not detrimentally effect the operation or results of the process to an intolerable degree and, preferably, has a relatively low overpotential for the halogen component of the zinc dihalide used. Such materials include graphite, platinum, palladium, gold and ruthenium oxide on titanium—the latter being preferred.

Temperatures/Pressures

Operation at ambient temperatures and atmospheric pressures is distinctly preferred. However, temperatures at least as high as the boiling point of bromine at the existing ambient pressure are preferred when the zinc dihalide is $ZnBr_2$.

Process Variables

The process variables most notably effecting the character of the zinc deposit are zinc dihalide concentration in the catholyte, kind and amount of other halides present in the catholyte, cathodic current density and catholyte flow rate. The experimental basis for the following discussions of these variables will be found in the Examples herein.

Effect of Zinc Dihalide Concentration in Catholyte

It has been found (see Example 1) that a more or less regular change in zinc morphology occurs when the content of zinc chloride (as the sole zinc salt) in the catholyte is increased from 1% ($\sim$0.07 molar) to 5% ($\sim$0.37) molar. In the 1-2% range, the deposit is black, powdery and easily and cleanly flushed off the cathode. At about 3%, the deposit is grey, feathery and is less cleanly removed, even after longer flushing at higher flow rates. At about 5%, the deposit is dendritic and vigorous, more prolonged flushing results in the dendrites breaking off to leave a rough textured zinc coating on the cathode surface. The particles flushed off after deposition from 1-2% solutions exhibit no crystalline structure observable at 80X magnification. The dendrites derived from $\sim$3% solutions are leaf-shaped crystals typically measuring about $9\mu \times 18\mu$. At 5%, the (unbroken) crystals are about $25\mu \times 50\mu$ in size.

Deposits formed from $\sim$10% zinc chloride solutions are more pronouncedly dendritic and larger but can still be broken off by a sufficiently vigorous swirling action of the catholyte stream. The zinc particles obtained at any concentration in the 1-10% range are effective reductants for the preparation of sym-tet from PCP and are believed highly suitable for other reductions.

Effect of Current Density

The changes (see Example 2) in the morphology of the zinc deposit caused by decreases in current density are similar to those caused by increases in $ZnCl_2$ concentration in the catholyte. At a density of 155 mA/cm$^2$, the zinc deposit is dark colored, powdery and non-adherent. At 39 mA/cm$^2$, the deposit is completely dendritic but can still be removed by flushing. Other tests have shown that flushable deposits are formed even at current densities of 170 mA/cm$^2$ and densities as low as about 165 mA/cm$^2$ are considered useful for present purposes. Densities as high as 330 mA/cm$^2$ have been employed with good results. Still higher densities are considered useful but not of further advantage. At densities of less than about 165 mA/cm$^2$ the deposit tends to form as an adherent layer. The most preferred density is 233 mA/cm$^2$ (about 1.5 A/in$^2$).

Effect of Catholyte Flow Rate—(See Example 3)

The only zinc deposits formed on the cathode when the catholyte is flowing are dendritic. The latter deposits are made up of shorter, coarser dendrites and become more so as the flow rate is increased, until the deposits are finally compact. At high current densities and high flow rate, compact, brittle deposits result. At low current densities and high flow rates, the deposits are compact and ductile.

Thus, intermittent catholyte flow is highly preferred. The optimum interval between flows will vary with cell design and other factors, such as the fraction passed of the theoretical total Coulomb requirement and the form of zinc deposit desired, and can readily be determined without resort to further invention. This is facilitated by use of a transparent backing member for the cathode in the cell used. As a guide, Coulomb fractions of from about 2% to about 3% of the theoretical requirement, between flows, were found suitable. Adequate flow durations ranged from a few seconds to several minutes, at flow rates of about 10 gpm (through the cathode chamber of the cell depicted in FIG. 1), as the zinc deposits changed from powders to well defined dendrite arrays.

Effect of a Supporting Electrolyte

Due to the relatively high cell voltages experienced in normal operation of the cell, experiments were conducted using various levels of sodium chloride in the catholyte as a supporting electrolyte. (See Example 4.) Although a two- to three-fold difference in solution conductivity results, operation of the cell with supporting electrolyte gave only a one to two volt decrease in cell voltage. Thus, the anolyte and membrane must make large contributions to the total cell voltage. As to the effect on zinc morphology, it was found that even at a magnification of 320X the zinc crystalline structure is difficult to define. Also, low current densities (0.25 A/in$^2$) gave fairly non-structured deposits as compared to the dendritic deposits obtained in the absence of sodium chloride. Although addition of sodium chloride does not greatly reduce the cell voltage, it does produce a consistently fine deposit of powdery zinc.

It is believed that other halides, such as alkali metal fluorides, chlorides as bromides or soluble alkaline earth such halides may be similarly employed as additives in the catholyte.

Effects of Lead Content in Zinc

At even low (10 ppm) lead contents, the zinc deposit is non-crystalline and easily flushed. At levels above 1000 ppm, the deposit is spongy and difficult to break up. However, the efficiency of the zinc when used to reduce PCP to sym-tet also increases. (This is discussed in more detail in the next section of these specifications.)

It should be noted that ease of removal of the zinc deposit from the cathode does not guarantee that further processing will not be needed (as by drying it or stirring it with a liquid) to convert it to a powder. This, however, can actually be an advantage in that particles separated from the cathodes as clumps or aggregates ("sponge") are more easily handled but will break up when added to an agitated mixture comprising water, a solvent and PCP. (The term "friable", as used herein, is not limited to deposits which come freely off the cathode as powders but does imply that grinding is not required to convert separated deposit portions (particle aggregates, "nodules" or "sponge fragments") to powders.

The present invention is not bottomed on a correct theoretical analysis of the physical/chemical phenomena involved but it is believed that it is the rate of zinc deposition, not the mass transfer rate within the catholyte, that governs the character of the deposit. That is, if the rate of deposition is less than the rate of mass transfer, the crystallinity of the deposit tends to increase but if the deposition rate exceeds the mass transfer rate, crystallinity tends to decrease.

The recovered zinc may be stored or used wet, as is convenient for reactions carried out in the presence of water, or may be dried first.

Use as Reductant of Zinc Powder Made by the Method of the Invention

It has been found that zinc powders prepared by the method of the present invention are uniquely reactive with PCP and water—at least in the presence of $ZnCl_2$—to form sym-tet and $Zn(OH)_2$. The $Zn(OH)_2$ precipitates and a high proportion of the PCP is converted to sym-tet. Introduction of HCl to the reaction mixture has no effect on the reduction rate and is apparently necessary only when the zinc has been air-dried. It is possible to write plausible equilibria for reactions between $ZnCl_2$ and water and/or $Zn(OH)_2$ which could provide small amounts of HCl. However, it is believed that not even catalytic amounts of HCl are generally required unless the zinc used has been allowed to dry in contact with oxygen (air). In that event an acid, such as HCl, apparently is required to initiate the reaction (activate the zinc).

Because PCP has a relatively high melting point (~130° C.) and it is highly desirable from the standpoints of flammability and toxicity to avoid the use of ordinary solvents, it is convenient to include sym-tet (melting point about 91° C.) to function as a solvent for the PCP. At about a 1 to 2 sym-tet to PCP ratio by weight, the mixture will be a homogeneous liquid at about 100° C. Surprisingly, no discernible reduction of sym-tet results.

The reduction may be carried out at any temperature at which the PCP is molten or dissolved and at which thermal degradation and/or other undesired reactions do not occur to an intolerable extent. Temperatures less than the initial boiling point of the reaction mixture at atmospheric pressure are highly preferred. At temperatures less than about 50° C., the reaction rate is low and more elevated temperatures, within the range of from about 65° to about 130° C., particularly from about 80° to about 100° C. are preferred. Solvents which reflux, at atmospheric pressures, at temperatures within the latter range include methanol and acetonitrile.

The reaction mixture may be worked up by any method conventionally employed for such mixtures. Since PCP and sym-tet can be separated from each other by distillation, a suitable procedure comprises filtration, separation of organic and aqueous phases (preceded by solvent extraction, if necessary) and stripping and fractional distillation of the organic phase.

If desired, HCl may be added even when wet zinc is used. Ordinarily, the acid will be added, after the reaction, to an essentially $Zn^o$—free decantate of a suspension of the $Zn(OH)_2$ in the liquid portion of the reaction mixture, to convert the $Zn(OH)_2$ to $ZnCl_2$. HCl of course can be metered in for the same purpose during the reaction, but at the possible expense of some zinc "loss" by reaction with the acid.

Although less desirable from the standpoints of flammability, toxicity and additional work-up steps, solvents such as lower alcohols, acetonitrile and aliphatic halocarbons—for example—may be employed at reflux at ambient pressures.

Effect of Lead Content in Zinc on PCP Reduction

The level of lead in electrogenerated zinc was changed from 50 ppm to 25,000 ppm in increments of 1000 to 5000 ppm (see Example 6). Very low lead levels (~50 ppm) gave low reaction efficiencies of PCP with zinc as well as low conversions. Most of the zinc in this case was presumably reacting with water (or HCl) to give hydrogen gas. When the lead level was increased to 1000 ppm, the reaction efficiency increased from 20% to about 50%. At 5000 to 10,000 ppm lead the efficiency for best runs ranged from 80 to 95%, and above 15,000 ppm greater than 90% of the zinc went toward PCP reduction. At a level of 25,000 ppm of lead, 99% of the zinc was utilized in sym-tet formation. Still higher lead contents are of course feasible but levels above 30,000 ppm are not seen as advantageous—at least for the reduction of PCP.

The full spectrum of uses for zinc powders in which lead contents of more than about 1000 ppm are advantageous has yet to be determined. However, it is believed that advantages may be realized in not only the use of zinc powders or dusts as reductants for a variety of substrate types but in various chemical, electrical and metallurgical applications as well.

Turning now to the drawings, reference should be had to FIGS. 1 and 1A. The cell (1) depicted therein is essentially the same as that employed in the examples described herein and comprises: a polyvinylidene fluoride (KYNAR; registered trade name of Pennsalt Co.) cathode backing plate (2) having an internally disposed, shallow, flat-bottomed, vertical positioning groove ((3); only upper end seen in FIG. 1) in which a 316 stainless steel cathode (4) is flush-fitted (in the assembled cell); a horizontally symmetrical, monolithic cathode spacer (5) having an inverted U shape and machined from a rectangular block of a transparent, acrylic plastic to form two spaced apart, parallel, vertical columns ((6); the "legs" of the "U") of rhomboid cross-section joined together and contiguous with a block ((7); only upper surface visible) at their upper ends, the bottom surface of block (7) and the inner surfaces of columns (6) (together with adjacent elements (4) and (10)) defining a vertical trough ((8); not visible in FIG. 1) closed at its upper end and having the cross-sectional shape of an isosceles trapezoid; a gasket (9) disposed between plate (2) and spacer (5); a separating membrane (10) formed from NAFION (registered trademark of E. I. duPont de Nemours for a hydrolyzed co-polymer of tetrafluoroethylene with a branched chain, vinyl-reactive oligomer of a perfluoroalkylene oxide having a fluorosulfonyl-substituent); a KYNAR anode-spacer (11) having the general shape of a rectangular letter O and defining an anolyte compartment ((12); not visible in FIG. 1); gaskets ((13 and (14)) on each side of the membrane (10); a ruthenium oxide on titanium anode plate (15) pierced by two vertically spaced apart, through bores ((16, (17)—not visible in FIG. 1) which communicate with compartment (12); a KYNAR anode backing plate (18) pierced by two bores ((19, (20); not visible in FIG. 1) which are co-axially aligned and register with bores (16) and (17), respectively; and a pair of gaskets (21) and (22) disposed on opposite sides of anode plate (15). The cathode backing plate (2) is pierced by a through-bore ((23); not shown in FIG. 1) which is co-axially aligned and registers with a bore ((24); not shown in FIG. 1) through the cathode, which opens into the upper end of trough (8). Bore (23) is tapped and has threaded into it a fitting (25) through which catholyte may enter trough (8)—which functions as the catholyte compartment (not separately numbered) in the cell. The cathode backing plate (2) is also pierced by a small diameter bore ((26); shown in phantom in FIG. 1) which is enlarged in diameter for part of its length and the enlarged portion ((27); also shown in phantom, in FIGS. 1 and 1A) is tapped to receive a fitting (28) which is threaded into it. A bore (29); also shown in phantom) through the cathode (4) is axially aligned and registers with the small end of bore (26) and permits insertion of a Luggin capillary through the fitting (28) to a point in the plane of the inner face of the cathode.

Bores (19) and (20) through the anode backing plate (18) are tapped and have threaded into them fittings (30) and (31), respectively, which function as the anolyte inlet and outlet connections to the cell. Bores (19) and (20) are aligned and register with bores (16) and (17) through the anode plate (15).

The upper ends of the cathode and anode plates protrude from the cell and are each pierced by a small bore ((32) and (33), respectively) to facilitate connection to negative and positive electrical leads (not shown).

The assembled cell is locked together by eight, stainless steel bolt (34) and nut (35) pairs. The bolts are disposed in as many through-bores (36); the bolts and bore walls on one side of the assembly are visible through the side of the nearest transparent column (6) and their non-visible portions are shown in phantom.

To ensure that the assembled cell is leak-tight, a thin layer of a sealant which does not set up too rapidly, such as, for example, an over-the-counter silastic, may be applied on the face of each gasket which will contact the element last or next-to-be-added to the developing assembly.

The catholyte enters the catholyte compartment through fitting (25) and exits through the open end (not visible in FIG. 1) of trough (8). The catholyte flow rate is adjusted as necessary to flush the deposited zinc off the cathode. By reason of the transparency of the cathode spacer (5), it is possible to tell—with the aid of backlighting—when flushing is required. This is optically facilitated by the rhomboid cross-sectional shape of the "columns"(6); note that the plane of the visible side of the nearest column intersects at an acute angle ($\beta$) the plane common to the nearest sides of the cathode and anode backing plates and the anode spacer.

As an option, the portion of gasket (9) in contact with cathode (4) can be eliminated and the block (7) may have cut out of the face of it next to the cathode a shallow groove which communicates with trough (8) and facilitates in-situ scraping off of stubbornly adherent zinc deposits which may form on the cathode during operating upsets. If desired, the resultant opening at the cell top can be closed by a slotted KYNAR cap which is slip-fitted over the cathode end (with a corresponding gasket) and removeably fastened (as by bolts turned into tapped bores) to the tops of the cathode backing plate and spacing plate (etc.). This was done in the experimental cell used in the examples given herein.

The gaskets (9), (13), (14), (21), (22) used are made of VITON (registered trademark of E. I. duPont de Nemours for a vinylidene fluoride/hexafluoropropylene copolymer).

FIG. 1A, as noted earlier herein, is an exploded view of the cell assembly of FIG. 1.

The four pair of holes shown in each of the plates and gaskets in FIG. 1A, together constitute (in the assembled cell) the through-bores numbered 36 in FIG. 1 and are not numbered in FIG. 1A.

As depicted in FIG. 1A, the anode spacer (11) is shown in a preferred form in which the portions of the spacer defining the anolyte compartment ends (which register with the anolyte inlet and outlet bores (19) and (20)) are shaped to also define shelf-like baffles ((37, (38)) which protect the membrane from the hydraulic forces developed by the entering and exiting anolyte flows. This has the effect of making the "face" of the anolyte space adjacent to the membrane somewhat smaller than the "face" adjacent the anode plate. (Alternatively, gasket (14) could by made with its central opening shorter than the full length of the anolyte compartment, thereby providing substantially the same protection for the membrane.)

Figure 2:
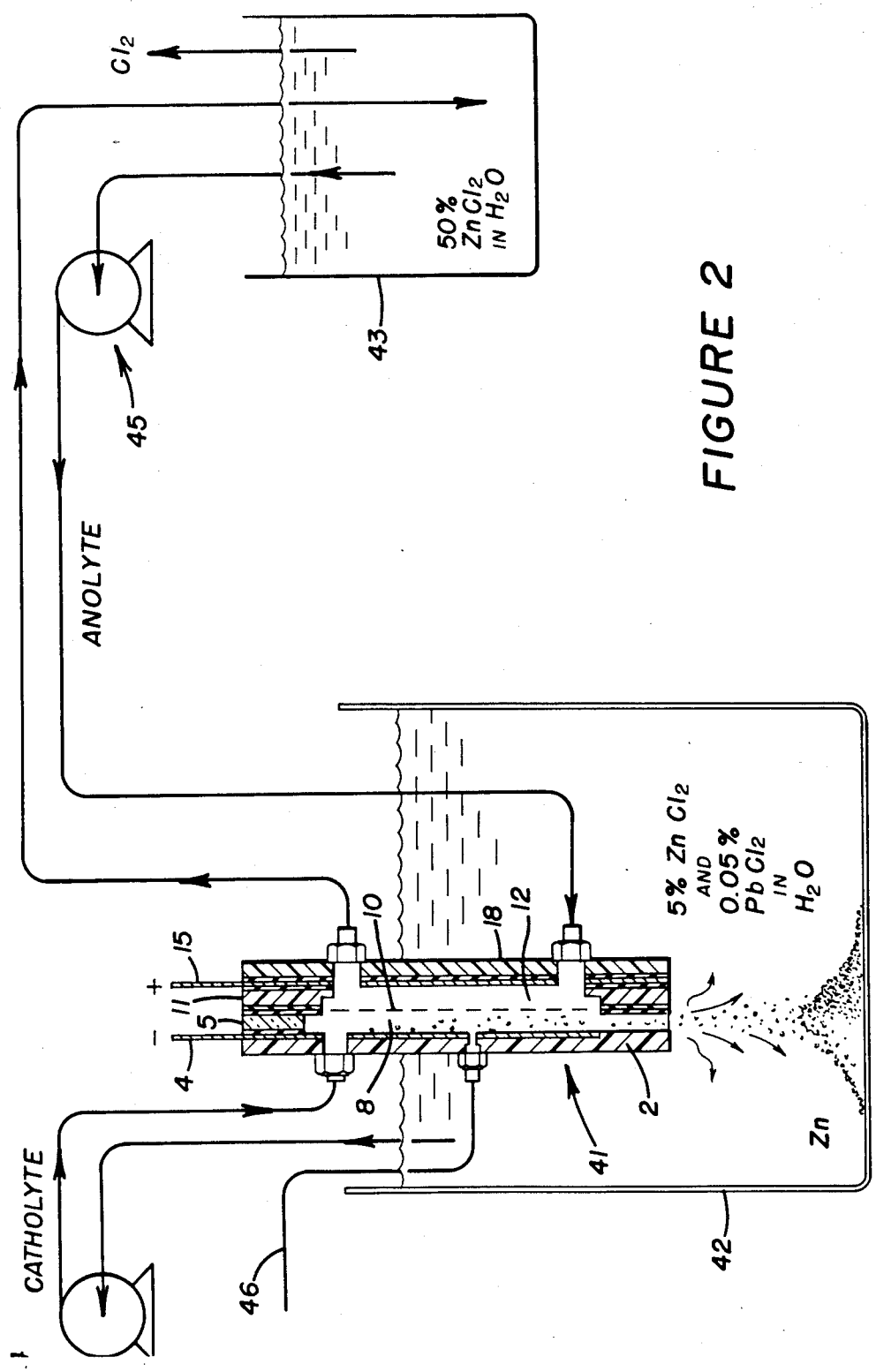
FIG. 2 is a semidiagramatic representation of an electrolysis system, including the cell of FIGS. 1 and 1A, for production of high lead content zinc.

FIG. 2 depicts in semi-schematic form the rudiments of an electrolytic system for production of "high lead zinc" by the method of the present invention. The system includes a cell (41), a catholyte reservoir and zinc receiver (42), an anolyte sump (43) which functions as a reservoir and as a means for separating the chlorine produced at the anode, catholyte and anolyte circulating pumps ((44) and (45), respectively) and a Luggin capillary (46). The catholyte pump is usually operated only intermittently, as required to flush zinc deposits off the cathode.

Cell (41) is shown (except for gaskets, bolts and fittings) in vertical, medial cross-section. The cell elements shown are numbered from left to right as in FIGS. 1 and 1A, as follows: cathode backing plate (2), cathode (4), cathode spacer (5), catholyte compartment (8), membrane (10), anode spacer (11), anolyte compartment (12), anode (15) and anode backing plate (18). The bores for the Luggin capillary, catholyte inlet and anolyte inlet/outlets are indicated but not numbered in the Figure.

The indicated catholyte and anolyte compositions are typical for production of high-lead zinc by the present method. The $PbCl_2$ content in the catholyte is such as to provide about 10,000 parts of Pb per million parts of Zn in the $Zn^o$ produced. By providing for removal of the zinc from the bottom of the catholyte reservoir, the process can be operated in a continuous mode indefinitely.

EXAMPLES

The following examples are for purposes of illustration and are not to be construed as limiting the present invention in a manner inconsistent with the claims in this patent.

The apparatus employed in carrying out the experiments described in the following Examples 1–4 was essentially that illustrated in FIG. 2. The catholyte and anolyte were prepared from solid $ZnCl_2$ (J. T. Baker, 99.4% pure) and distilled water. The $ZnCl_2$ concentration was varied as indicated in the catholyte but was held at 35% (2.57 M) in the anolyte. The experiments were run at constant current with an HP6264B D.C. power supply (20 amps at 20 volts maximum output) controlled by a computer responsive to the cathode potential determined by means of a saturated calomel reference electrode and the Luggin capillary. During a run, the cathode potential typically varied from $-2.0$ V to $-1.2$ V, depending on the extent of zinc deposition on the cathode surface. Deposited zinc was removed by flushing and—when necessary—by scraping (through an opening in the top of the catholyte compartment, an option described earlier herein but not illustrated in FIG. 2). Samples of the zinc deposits were examined by light microscopy.

Example 1—Effect of $ZnCl_2$ Concentration in Catholyte

Otherwise essentially identical runs were carried out at each of four different $ZnCl_2$ concentrations. The run conditions are tabulated below.

| | |
|---|---|
| $ZnCl_2$ in catholyte: | 1%, 2%, 3%, 5%. |
| $ZnCl_2$ in anolyte: | 35%. |
| Current Density: | 1000 mA/in$^2$ (155 mA/cm$^2$). |
| Catholyte flow rate: | 0 |
| Anolyte flow rate: | 0.5 gpm (1.89 liters/m) Reynolds No. ~2000. |

The zinc deposits transformed from black powdery aggregates at 1% to 2% $ZnCl_2$, to grey feathery deposits at 3% $ZnCl_2$, to a silvery dendritic growth at 5% $ZnCl_2$. Crystalline structures first appeared as tiny silvery specks in the 3% solutions and developed into leaf-shaped structures in the 5% $ZnCl_2$ deposits.

All the zinc deposits generated in this study were removed by the jet-stream method, but longer flushing times and higher catholyte flow rates were required for the removal of deposits in 3% and 5% $ZnCl_2$ solutions. In the case of 5% $ZnCl_2$ deposits, dendrites tended to break off from their basal parts under high flow condition in the cathode compartment. Thus, a rough surface of residual zinc was left on the surface after flushing.

For the 1% and 2% ZnCl solutions, flushing removed virtually all the zinc metal from the cathode surface.

Microscopic examination of deposit samples at 80× magnification revealed that a structural transition had occurred between the use of 2% and 3% $ZnCl_2$ solutions. Zinc deposited in 1% and 2% $ZnCl_2$ solutions contained no observable crystalline structure. When the concentration of $ZnCl_2$ was increased to 3%, tiny leaf-shape crystals began to appear. A typical crystal from the 3% solution measured $18\mu$ by $9\mu$. As the $ZnCl_2$ concentration was increased to 5%, the crystal size increased to approximately $50\mu$ by $25\mu$.

The data generated in the preceding experiment is summarized in Table I.

TABLE I

ZINC DEPOSITION DATA

| $ZnCl_2$ Concentration (Aq. %) | Current Density (A/in$^2$) | Current Efficiency[a] (%) | Cathode Potential[b] (V vs. SCE) | Cell Potential (V) | Type of Zinc Deposited |
|---|---|---|---|---|---|
| 1 | 1.0 | 94 | [c] | 20 | — |
| 1 | 0.75 | 91 | $-1.17$ | 14 | Powdery |
| 1 | 0.50 | 91 | $-1.5$ | 12.5 | Powdery |
| 1 | 0.25 | 73 | $-1.55$ | 7.3 | Powdery |
| 2 | 1.0 | 95 | $-2.14$ | 17 | Powdery |
| 2 | 0.75 | 92 | $-1.2$ | 12 | Powdery |
| 2 | 0.50 | 90 | $-2.1$ | 9.0 | Dendritic |
| 2 | 0.25 | 83 | $-1.7$ | 5.8 | Dendritic |
| 3 | 1.0 | 92 | $-1.4$ | 15 | Powdery/Dendritic |
| 3 | 0.75 | 92 | $-1.24$ | 10 | Dendritic |
| 3 | 0.50 | 90 | $-1.32$ | 7.6 | Dendritic |
| 3 | 0.25 | 78 | $-1.36$ | 5.45 | Dendritic |
| 5 | 1.0 | 82 | $-1.4$ | 11.6 | Dendritic |
| 5 | 0.75 | 76 | $-1.3$ | 8.8 | Dendritic |
| 5 | 0.50 | 80 | $-1.12$ | 6.5 | Compact |
| 5 | 0.25 | 80 | $-1.2$ | 4.8 | Compact |

NOTES:
[a]High current efficiencies (90%) were typically observed in the several runs after cleaning the cathode and membrane.
[b]Cathode potential was very sensitive to Luggin placement and zinc deposition.
[c]At 1.0 A/in$^2$ in 1% $ZnCl_2$ the cell voltage exceeded the rectifier output voltage.

Example 2—Effect of Current Density

In this study, experiments were conducted at a catholyte $ZnCl_2$ concentration of 2% and at four different current densities: 1000 mA/in$^2$, 750 mA/in$^2$, 500 mA/in$^2$ and 250 mA/in$^2$. Since the cathode had a fixed area of 4.5 in$^2$, the currents passed through the cell were 4.5 A, 3.37 A, 2.25 A, and 1.12 A, respectively. The anolyte flow rate was 0.5 gpm (Reynolds No. ~2000) and the catholyte did not flow.

In general, morphological transformations resulting from decreasing current density were similar to those observed for increasing the $ZnCl_2$ concentration at constant current. At 1000 mA/in$^2$ (155 mA/cm$^2$) a dark, nonadherent layer of powdery zinc was deposited. When the current density was lowered to 750 mA/in$^2$ (116 mA/cm$^2$), cylindrical aggregates of powdery zinc were formed, and at 500 mA/in$^2$ (78 mA/cm$^2$) dendritic growth began to appear. Since the deposit was a mixture of powdery and crystalline zinc, the thin and fragile zinc was covered with clusters of powdery zinc. Finally, at 250 mA/cm$^2$ (39 mA/cm$^2$), the zinc deposit turned completely dendritic (but could be flushed off the cathode).

The ease of resolving zinc deposits from the cell followed the same trend observed in the previous example. Powdery deposits were easily removed with quick light flushes and dendritic deposits required high flow rates for extended periods of time. Also, after flushing, dendritic growths left a rough layer of adherent zinc on the cathode surface.

In contrast to the more abrupt change that took place between 2% and 3% ZnCl$_2$ deposits, a gradual change from a powdery to a crystalline deposit was observed in going from 1000 mA/in$^2$ to 500 mA/in$^2$. Microscopic examination of the deposit generated at 750 mA/in$^2$ showed a mixture of amorphous and crystalline structures. The crystals formed at 500 mA/in$^2$ were approximately the same size as those formed from 3% ZnCl$_2$ solutions.

Example 3—Effect of Catholyte Flow Rate

It was observed during runs conducted in a flowing catholyte that no powdery zinc was deposited on the cathode under any of the ZnCl$_2$ concentrations or current densities employed. Also, the dendritic zinc formed was shorter and coarser than that formed under no-flow conditions. Finally, compact zinc formation began to take place at very high flow rates (3 gal./min. through a cell as depicted in the drawings and having external dimensions of about 2"×2½"×9½" (~5×64×~24 cm).

The degree of difficulty in removing the dendritic deposits increased with increasing flow rate. In most cases, dendrites had to be scraped from the cathode surface. Under high flow and high current density conditions, 3 gpm and 1000 mA/in$^2$, respectively, the compact zinc deposit was brittle and broke apart quite easily. As the current density was lowered to 250 mA/in$^2$, the compact zinc became ductile and remained in one piece as it was scraped off the cathode. The reaction conditions are tabulated below.

| | |
|---|---|
| ZnCl$_2$ in catholyte: | 2%, 3%, 5%. |
| ZnCl$_2$ in anolyte: | 35%. |
| Current densities: | 750 mA/in$^2$; 250 mA/in$^2$. |
| Catholyte flow rates: | 0.5, 1 and 3 gpm. |
| Anolyte flow rate: | 0.5 gpm. |

Example 4—Effects of Lead Content on Zinc; Morphology and Ease of Removal from Cathode Most of the zinc powder generated in the study was used in reducing PCP to sym-tet. Since leaded zinc had been found essential for an efficient PCP to sym-tet reaction, the effects of lead in the catholyte on the morphology of zinc deposits was investigated. Four different lead levels were examined: 10 ppm, 1,000 ppm, 5,000 ppm, and 10,000 ppm. Two current densities were tried at 10,000 ppm lead in order to see how lead impurity would influence the current density effects on morphology. Conditions for these experiments are listed below.

All the zinc deposits generated in this study were non-crystalline in nature and were easily (non-dendritic) removed from the cathode surface with a flow of catholyte. Deposits with lead levels over 1,000 ppm were very spongy and more difficult to break apart. The color of the zinc also changed from black to light grey as the lead level was increased.

Microscopic photographs of the leaded zinc showed all the deposits to consist of very small particles. Also, changing the current density in a highly leaded catholyte (10,000 ppm Pb) gave very little change in the zinc morphology. The deposits stayed spongy and amorphous even after the current density was reduced by 50%.

| | |
|---|---|
| ZnCl$_2$ in catholyte: | 2%. |
| ZnCl$_2$ in anolyte: | 35%. |
| Current densities: | 750 mA/in$^2$; 250 mA/in$^2$. |
| Catholyte flow rate: | 0. |
| Anolyte flow rate: | 0.5 gpm. |
| Parts Pb per million parts Zn in catholyte: | 10, 1000, 5000, 10,000. |

Example 5—Effect of Lead Content on Efficiency of Zinc as a Reductant for PCP The following experiment was carried out after it was found that zinc electroregenerated from ZnCl$_2$ solutions (and having a lead content of 50 ppm) was significantly less efficient than reagent grade zinc (400 ppm lead) in the reduction of PCP to sym-tet.

Procedure

Into a 100 ml round bottom flask were placed 5 g PCP, 2.5 g sym-tet, and 15 ml of 12% aqueous ZnCl$_2$, and 3.0 g of electrogenerated zinc. This mixture was heated with a silicone oil bath and hot plate to 100° C. where the PCP/sym-tet mixture became molten. At this time, one equivalent of 3 M HCl was slowly added to the reaction mixture. When the reaction was completed, the organic material was dissolved in 25 ml of methylene chloride and the unreacted zinc was filtered and weighed. The organic phase was separated and concentrated to leave the isolated product as a white solid. From the weight of zinc remaining after reaction and the weight of isolated product, the reaction efficiency and isolated yield were calculated, respectively (Table I).

The progress of each reaction was followed by HPLC (High Performance Liquid Chormatography). A 15 cm, 5µ, C-18 column was used at 40° C. with a flow of 1 ml/min. of 93% methanol/7% water. The U.V. detector was set at 300 nm and, typically, sym-tet and PCP eluted at 3.5 and 4.5 minutes, respectively.

Since wet zinc was used in many of the experiments, a method had to be devised to weigh wet zinc in order to obtain a zinc mass balance. This was accomplished by weighing the wet zinc in a specific volume of water and comparing this weight with that of water alone. From the density of water and zinc, one can calculate the weight of zinc (±5%).

Electrogenerated zinc was produced in a cell essentially as shown in the drawings. The lead levels in the zinc were adjusted by dissolving lead chloride into the zinc chloride catholyte solution to provide from 50 to 25,000 parts of lead per million parts of zinc. Assuming that the rates of lead and zinc deposition are the same, the lead level in electrodeposited zinc should be very close to that in solution. Analytical results supported this assumption.

Lead Content in Zinc

The level of lead in the electrogenerated zinc was changed from about 30 ppm to 25,000 ppm in increments of 1000 to 5000 ppm (see Table II). The lowest lead level (up to 50 ppm) gave a low reaction efficiency for the reduction of PCP with zinc, as well as low conversions. When the lead level was increased to 1000 ppm, the reaction efficiency increased from 20% to about 50%. At 5000 to 10,000 ppm lead the efficiency for best runs ranged from 80 to 95%, and above 15,000 ppm greater than 90% of the zinc went toward PCP reduction.

Wet vs. Dry Zinc

A comparison was made in the reactivity of wet, air dried and vacuum dried zinc toward PCP (Table II). Wet zinc was transferred directly from the electrolysis cell to a reactor without treatment. Air dried zinc was prepared by washing the electrogenerated zinc several times with water followed by several washings with acetone. After allowing the zinc to dry in air, the zinc was used in reduction reactions. Vacuum dried zinc was washed the same as air dried zinc, dried in vacuo, and stored under argon. The overall results of this comparison do not unequivocally support a generalization in this regard. However, the results of runs 5 and 6 suggest that the use of the air dried zinc requires addition of an acid. It would also appear that the use of a zinc powder which has been kept wet since it was formed is preferable.

Presence or Absence of HCl

It was originally assumed that HCl addition was essential to the reaction in all cases. However, with the apparent exception of use of air dried zinc, this assumption proved incorrect. Parallel reactions with and without HCl (using wet zinc) were found to proceed at the same rate. The efficiency of the reaction (as measured by the ratio of sym-tet produced to the zinc consumed) appears to be generally the same (at least as long as the acid is added at a low enough rate to be rapidly consumed in neutralizing or preventing formation of $Zn(OH)_2$).

TABLE II

| Run # | Added HCl | ppm Pb in Zn | Type of Zinc | % Conversion | Isolated Yield | Zn Reaction Efficiency |
|---|---|---|---|---|---|---|
| 1 | Yes | 30 ± 20[b] | (Dry) | 32 | 94 | 22 |
| 2 | Yes | 1000 | (Wet) | 99 | 99 | 46 |
| 3 | Yes | 1000 | (Wet) | 99 | 73 | 51 |
| 4 | Yes | 1000 | (Air Dry) | 47 | 38 | 29 |
| 5 | No | 1000 | (Air Dry) | NR[c] | NR | NR |
| 6 | No | 1000 | (Wet) | 95 | 80 | — |
| 7 | Yes | 3000 | (Air Dry) | 36 | 94 | 17 |
| 8 | Yes | 3000 | (Wet) | 91 | 93 | 35 |
| 9 (L)[a] | Yes | 3000 | (Wet) | 52 | 99 | 57 |
| 10 | Yes | 5000 | (Air Dry) | 91 | 91 | 28 |
| 11 | Yes | 5000 | (Wet) | 96 | 93 | 92 |
| 12 | Yes | 5000 | (Vac. Dry) | 71 | 96 | 55 |
| 13 (L) | Yes | 5000 | (Wet) | 55 | 95 | 92 |
| — | No | 5000 | (Wet) | 93 | 91 | 94 |
| 14 | Yes | 6000 | (Air Dry) | 99 | 99 | 81 |
| 15 | Yes | 6000 | (Wet) | 99 | 80 | 36 |
| 16 | Yes | 7000 | (Dry) | 98 | 87 | 66 |
| 17 (L) | Yes | 7000 | (Wet) | 70 | 73 | 73 |
| 19 | No | 7000 | (Wet) | 99 | 80 | 80 |
| 20 | Yes | 7000 | (Dry) | 98 | 86 | 58 |
| 22 | No | 10,000 | (Wet) | 99 | 80 | 80 |
| 23 (L) | Yes | 10,000 | (Wet) | 70 | 73 | 73 |
| 24 | No | 15,000 | (Wet) | 99 | 86 | 99 |
| 25 | No | 20,000 | (Wet) | 94 | 76 | 87 |
| 26 | No | 25,000 | (Wet) | 95 | 66 | 99 |

NOTES FOR TABLE II:
[a]Runs 9, 13, 17 and 23 were run with zinc as the limiting reagent as indicated by an L.
[b]Limit of accuracy of analytical method used.
[c]No reaction.

What is claimed is:

1. A method of preparing lead-containing, zinc powders which, when wet, do not require the presence of an acid in order to function as a reductant in the conversion of pentachloropyridine to 2,3,5,6-tetrachloropyridine, said method comprising:

a. providing an electrolytic cell which includes a cathode, an anode and an ion-permeable or porous member separating the cell into cathode and anode compartments, b. charging to the anode compartment an from about 1.5 to about 5 molar aqueous zinc dihalide solution and changing to the cathode compartment an from about 0.07 to about 0.7 molar aqueous zinc dihalide solution containing from about 1000 to about 30,000 parts by weight of lead ions per million parts of zinc, and c. applying across said cell a D.C. potential such as to establish and maintain a cathode potential within the range of from about −2 to about −1 volts, relative to a saturated calomel reference electrode and a cathodic current density of about 165 or more $mA/cm^2$, thereby forming at the cathode a friable zinc deposit which can be removed by impingement thereon of a flowing liquid.

2. The method of claim 1 wherein the zinc dihalide in the anolyte is the same as that in the catholyte.

3. The method of claim 1 wherein the anolyte is from about 2 to about 3 molar in the zinc dihalide.

4. The method of claim 1 wherein the catholyte is from about 0.1 to about 0.2 molar in the zinc dihalide and, optionally, includes an ionizeable halide other than said dihalide.

5. The method of claim 1 wherein the current density is not greater than 330 $mA/cm^2$.

6. The method of claim 1 in which the catholyte is intermittently caused to flow past and impinge against said zinc deposit with a force sufficient to remove it from the cathode.

7. The method of claim 1 wherein the zinc dihalide is $ZnCl_2$.

8. The method of claim 1 in which the cathode is stainless steel or aluminum.

9. The method of claim 1 wherein the anode is ruthenium oxide on titanium.

10. The method of any of claims 1, 2, 3, 4, 5, 6, 7, 8 and 9 wherein the content of lead ions in the catholyte is from about 5000 to about 25,000 parts by weight per million parts of zinc.

11. The method of any of claims 1, 2, 3, 4, 5, 6, 7, 8 and 9 wherein the content of lead ions in the catholyte is from about 15,000 to about 25,000 parts by weight per million parts of zinc.

12. The method of claim 2 wherein the zinc dihalide is $ZnCl_2$, the $ZnCl_2$ concentrations in the catholyte and anolyte are from about 0.1 to about 0.2 molar and from about 2 to about 3 molar, respectively, the cathodic current density is not greater than 330 mA/cm$^2$, the cathode is stainless steel or aluminum, the anode is ruthenium oxide on titanium, the content of lead ions in the catholyte is within the range of from about 15,000 to about 25,000 parts by weight per million parts of zinc and the catholyte is intermittently caused to flow past and impinge on said zinc deposit, thereby removing it from the cathode.

13. The method of claim 12 wherein $Cl_2$ is produced at the anode, the anolyte is continuously passed through the cell and, together with said $Cl_2$, to a reservoir, where the $Cl_2$ is allowed to separate, and the anolyte is returned to the cell, and the catholyte, while flowing in said manner to remove the zinc deposit, is passed out of the cell with the removed zinc to a settling zone, is separated from the zinc in that zone and is returned to the cell.

14. The method of preparing 2,3,5,6-tetrachloropyridine from pentachloropyridine which comprises contacting the latter compound in an aqueous zinc chloride reaction medium with a zinc powder, the particles of which consist essentially of zinc but include more than 1000 parts of lead per million parts of the zinc.

15. The method of claim 14 wherein said zinc particles have been formed wet and kept wet since formed.

16. The method of claim 14 wherein said zinc particles have been air dried and HCl is added in an amount sufficient to cause the reaction to proceed.

17. The method of claim 14 wherein the reaction medium includes a solvent for the pentachloropyridine and has an initial boiling point of from about 80° to about 100° C. at a pressure of 760 mmHg.

18. The method of claim 15 wherein said solvent is 2,3,5,6-tetrachloropyridine and is employed in the amount of about 1 part by weight per 2 parts of pentachloropyridine charged to the reaction.

19. The method of any of claims 14, 15, 16, 17 and 18 wherein said particles contain from about 5000 to about 30,000 parts by weight of lead per million parts of zinc.

20. The method of any of claims 14, 15, 16, 17 and 18 wherein said particles contain from about 15,000 to about 25,000 parts of lead per million parts of zinc.

* * * * *

UNITED STATES PATENT AND TRADEMARK OFFICE
CERTIFICATE OF CORRECTION

PATENT NO. : 4,724,051
DATED : February 9, 1988
INVENTOR(S) : Theodore J. Sobieralski It is certified that error appears in the above-identified patent and that said Letters Patent is hereby corrected as shown below:

Col. 3, line 4, after "(2)", insert -- the --;

Col. 3, line 8, "dihalide" has been misspelled;

Col. 4, line 54, after "and" delete "4HO-" and insert -- 4OH- --;

Col. 7, line 28, delete "Zn(QH)$_2$" and insert -- Zn(OH)$_2$ --;

Col. 10, line 26, delete "by" and insert -- be --;

Col. 12, line 64, delete "resolving" and insert -- removing --;

Col. 14, line 37, "Chromatography" has been misspelled.

Signed and Sealed this

Twentieth Day of December, 1988

*Attest:*

DONALD J. QUIGG

*Attesting Officer*  *Commissioner of Patents and Trademarks*